United States Patent [19]

Mori et al.

[11] Patent Number: 5,738,718
[45] Date of Patent: Apr. 14, 1998

[54] ZINC OXIDE-CONTAINING SPHERICAL SILICA AND PROCESS FOR ITS PRODUCTION

[75] Inventors: Hiroo Mori; Hiroshi Funaki; Kunihiko Terase; Hachirou Hirano, all of Ichihara, Japan

[73] Assignee: Asahi Glass Company Ltd., Tokyo, Japan

[21] Appl. No.: 833,427

[22] Filed: Apr. 7, 1997

Related U.S. Application Data

[63] Continuation of Ser. No. 537,275, Sep. 29, 1995, abandoned.

[30] Foreign Application Priority Data

Sep. 30, 1994 [JP] Japan ................. 6-237826
Sep. 30, 1994 [JP] Japan ................. 6-237827

[51] Int. Cl.$^6$ ........................................ C01B 33/12
[52] U.S. Cl. ................... 106/481; 106/492; 423/338; 423/339
[58] Field of Search ................... 423/338, 339; 106/481, 492; 424/59, 724, 641, 401

[56] References Cited

U.S. PATENT DOCUMENTS

| | | | |
|---|---|---|---|
| 3,928,540 | 12/1975 | Morgan | 423/339 |
| 4,090,887 | 5/1978 | Marquisee et al. | 106/309 |
| 4,132,560 | 1/1979 | Marquisee et al. | 106/492 |
| 4,216,113 | 8/1980 | Winyall | 423/338 |

FOREIGN PATENT DOCUMENTS

| | | |
|---|---|---|
| 0 679 382 | 11/1995 | European Pat. Off. |
| 2 333 032 | 6/1977 | France |
| 58-125609 | 7/1983 | Japan ................. 423/338 |

OTHER PUBLICATIONS

Database WPI, Derwent Publications, AN 91-277659, JP-A-3 183 620, Aug. 9, 1991.
Database WPI, Derwent Publications, AN 92-120434, JP-A-4 065 312, Mar. 2, 1992.
Database WPI, Derwent Publications, AN 94-188691, JP-A-6 127 932, May 10, 1994.
Database WPI, Derwent Publications, AN 94-115035, JP-A-6 064 915, Mar. 8, 1994.
Database WPI, Derwent Publications, AN 84-117209, JP-A-59 054 619, Mar. 29, 1984.

*Primary Examiner*—Melissa Bonner
*Attorney, Agent, or Firm*—Oblon, Spivak, McClelland, Maier & Neustadt, P.C.

[57] ABSTRACT

A process for producing zinc oxide-containing spherical silica, which comprises emulsifying, in an organic solvent containing a surfactant, a dispersion having zinc oxide with a particle size of from 0.005 to 0.5 μm dispersed in an aqueous alkali metal silicate solution in an amount of from 10 to 70 wt % based on the total amount of zinc oxide and $SiO_2$ in the aqueous alkali metal silicate solution, followed by gelation of the resulting emulsion with carbon dioxide gas.

9 Claims, No Drawings

ZINC OXIDE-CONTAINING SPHERICAL SILICA AND PROCESS FOR ITS PRODUCTION

This application is a Continuation of application Ser. No. 08/537,275, filed on Sep. 29, 1995, now abandoned.

The present invention relates to zinc oxide-containing spherical silica, particularly zinc oxide-containing spherical silica having ultraviolet ray-shielding ability, which is useful as e.g. a material for cosmetics, an additive to coating materials or an additive to resins.

As an ultraviolet ray-shielding agent, zinc oxide has been used as a material for cosmetics, a resin additive, an additive to coating materials or a component of a coating agent for e.g. glass.

For the purpose of improving the transparent touch and the ultraviolet ray-shielding effect, it has been attempted to make particles very fine. For example, a cosmetic containing very fine particles of zinc oxide having the maximum particle size of at most 0.1 µm and an average particle size of from 10 to 60 nm (Japanese Unexamined Patent Publication No. 231607/1985), a cosmetic composition containing zinc oxide having an average particle size of at most 20 nm (Japanese Unexamined Patent Publication No. 84017/1987), a cosmetic containing zinc oxide having an average particle size of from 70 to 300 nm (Japanese Unexamined Patent Publication No. 228006/1987) and a coating composition having zinc oxide with a particle size of at most 0.1 µm dispersed (U.S. Pat. No. 5,039,320) have been disclosed.

However, finely pulverized zinc oxide tends to agglomerate, and it has been difficult to incorporate it in a finely dispersed state. The activity tends to be strong as the specific surface area increases, whereby it tends to decompose an organic component incorporated together. In order to improve the dispersibility, a pigment has been proposed which has fine particles of zinc oxide fixed on the surface of a carrier by a binder (Japanese Unexamined Patent Publication No. 119418/1988). Further, in order to suppress the decomposing activity, zinc oxide with its surface coated by an oxide of e.g. Al or Si, has been proposed (Japanese Unexamined Patent Publication No. 183620/1991).

However, the one having zinc oxide fixed on the surface of a carrier has a problem that the activity is high and the flowability is poor since zinc oxide is exposed on the surface. On the other hand, the one having fine particles of zinc oxide coated with another metal oxide retains the original shape of zinc oxide, and accordingly it has a problem that the flowability is low, and when incorporated to a cosmetic, it gives a poor feeling on use.

Further, a method for producing spherical silica by gelling with an acid a silicate having a pigment dispersed therein, is disclosed in U.S. Pat. No. 4,090,887, and spherical silica containing a pigment is disclosed in U.S. Pat. No. 4,132,4560. However, from the viewpoint of the ultraviolet ray-shielding performance, the reaction conditions, etc. are not appropriate, and such spherical silica is not necessarily suitable for use as a ultraviolet ray-shielding material.

It is an object of the present invention to provide a ultraviolet ray-shielding material which has high ultraviolet ray-shielding performance and which provides excellent smoothness and flowability and a high transparent touch when incorporated to e.g. cosmetics.

The present invention provides a process for producing zinc oxide-containing spherical silica, which comprises emulsifying, in an organic solvent containing a surfactant, a dispersion having zinc oxide with a particle size of from 0.005 to 0.5 µm dispersed in an aqueous alkali metal silicate solution in an amount of from 10 to 70 wt % based on the total amount of zinc oxide and $SiO_2$ in the aqueous alkali metal silicate solution, followed by gelation of the resulting emulsion with carbon dioxide gas.

Now, the present invention will be described in detail with reference to the preferred embodiments.

The particle size of zinc oxide is required to be from 0.005 to 0.5 µm. If the particle size exceeds 0.5 µm, the ultraviolet ray-shielding effect tends to be low, such being undesirable. Also in a case where the particle size is less than 0.005 µm, the ultraviolet ray-shielding effect tends to be low, and the wavelength region which can be shielded, tends to shift towards a short wavelength side, such being undesirable. More preferably, the average particle size of zinc oxide is from 0.02 to 0.3 µm.

The content of zinc oxide in the aqueous alkali metal silicate solution is suitably from 10 to 70 wt % based on the total amount of zinc oxide and $SiO_2$ in the aqueous alkali metal silicate solution. If the content of zinc oxide is less than 10 wt %, the ultraviolet ray-shielding effect tends to be inadequate, such being undesirable. If the content of zinc oxide exceeds 70 wt %, it tends to be difficult to obtain spherical silica, and the transmittance of visible light tends to be low, whereby the product will be unsuitable for e.g. cosmetics.

In the aqueous alkali metal silicate solution, the alkali metal is not particularly limited, but sodium is most preferred from economical reasons. With respect to the proportions of silicic acid and the alkali metal, when the alkali metal is sodium, the molar ratio of $SiO_2/Na_2O$ is preferably from 2.0 to 3.5. The concentration of the aqueous solution is preferably from 5 to 30 wt % as $SiO_2$.

Zinc oxide can be dispersed in the aqueous alkali metal silicate solution by means of e.g. a high speed shear homogenizer, a media mill or an ultrasonic homogenizer. Further, a dispersing agent may optionally be used.

As the organic solvent, a substance capable of dissolving carbon dioxide gas therein is preferred. For example, an aliphatic hydrocarbon such as hexane or octane, an aromatic hydrocarbon such as xylene or toluene, a chlorinated hydrocarbon such as chloroform, trichloroethylene or tetrachloroethylene, or a chlorofluorocarbon such as trichlorotrifluoroethane, dichlorotrifluoroethane, dichlorofluoroethane or dichloropentafluoropropane, is preferred.

As the surfactant, a polyethylene glycol fatty acid ester, a polyoxyethylene alkylphenyl ether, a polyoxyethylene alkyl ether, a sorbitan fatty acid ester or a polyoxyethylene sorbitan fatty acid ester is preferred. The amount is preferably from 0.05 to 10 wt %.

The surfactant is dissolved in the organic solvent, and an aqueous alkali metal silicate solution having zinc oxide dispersed, is added thereto for emulsification. It is preferred that the aqueous solution is added to the organic solvent in a volume ratio within a range of from 0.1 to 1, so that a W/O type emulsion will be formed. Emulsification is preferably conducted by means of e.g. a turbine agitator or a high speed shear emulsifier. In the emulsion, the particles of the aqueous alkali metal silicate solution preferably have an average particle size of from 0.1 to 10 µm.

Then, by introducing carbon dioxide gas into the emulsion, the aqueous alkali metal silicate solution is gelled. In the present invention, gelation is carried out in an emulsified state, spherical silica gel can be obtained. Zinc oxide will be gelled while maintaining the state as dispersed in the aqueous solution, and will thus be dispersed in a silica gel matrix.

For the gelation, it is preferred to introduce carbon dioxide gas under such a condition that the initiation time for gelation will be at least 4 minutes. When carbon dioxide gas is introduced into the emulsion, at some point of time, it will be clearly observed even visually that the viscosity of the emulsion increases rapidly and clearly, and such a point of time is regarded as the initiation time for gelation. If the initiation time for gelation is shorter than 4 minutes, the dispersed state of zinc oxide in the resulting silica gel particles is not proper, and the ultraviolet ray-shielding effect tends to be poor, such being undesirable. The initiation time for gelation can be adjusted by changing e.g. the flow rate or partial pressure of the carbon dioxide gas. More preferably, the initiation time for gelation is at least 5 minutes.

After completion of the gelation, the organic solvent is removed, and heat treatment or reagent treatment is optionally applied to obtain an aqueous slurry of zinc oxide-containing spherical silica (hereinafter referred to as a slurry immediately after preparation). The slurry immediately after preparation contains mainly zinc oxide-containing spherical silica and an alkali metal carbonate, and the zinc oxide-containing spherical silica is separated and then optionally washed and dried.

When the silica is to be used as a material for cosmetics or as an additive to a resin or coating material, it is desirable that the pH of a dispersion having the zinc oxide-containing spherical silica dispersed in water (in this specification, the pH of a 10 wt % slurry obtained by dispersing the silica in water, and it will hereinafter be referred to simply as the pH of silica) is about neutral at a level of from 7 to 9. More preferably, the pH is from 7 to 8. In the case of usual silica, the pH of silica can be made to a level of 7 by adding an acid to a silica slurry to bring the pH to a level of not higher than 6, followed by filtration and washing. However, in the case of silica containing zinc oxide, if the pH is brought to a level of not higher than 6, zinc oxide will dissolve, and its content will decrease, and not only that, a substantial cost will be required for treatment of the waste liquid. However, if the following washing methods are employed, the pH of silica can be brought to a level of from 7 to 8 without substantially changing the content of zinc oxide, and such methods are preferred.

The first method is a method wherein the silica slurry immediately after preparation is filtered and then washed with water having carbon dioxide gas dissolved therein, under atmospheric pressure or an elevated pressure until the predetermined purity is attained. Carbon dioxide gas is preferably saturated, but may be not saturated. The pH of water having carbon dioxide gas dissolved therein is preferably within a range of from 3.3 (when saturated) to 4. If dilute hydrochloric acid, dilute sulfuric acid or dilute nitric acid having the same level of pH is used, it is not possible to obtain silica having the desired pH, and such is inappropriate.

The second method is a method in which carbon dioxide gas is blown into the slurry immediately after preparation to bring the pH to a level of from 5 to 7, followed by filtration. This operation is preferably repeated more than once until the desired purity can be attained.

Although the mechanism is not known, when the alkali metal silicate is gelled by carbon dioxide gas, gelation of silica appears to proceed under a condition favorable to the dispersed state of zinc oxide. The carbon dioxide gas is believed to be once dissolved in the organic solvent and then react with the alkali metal silicate.

Further, it is believed that by washing with water having carbon dioxide gas dissolved therein or by blowing carbon dioxide gas into the silica slurry, hardly soluble carbonate of zinc is formed, whereby only impurities such as sodium can selectively be removed by washing, and the pH of silica can be made substantially neutral, and elution of zinc can be suppressed.

The zinc oxide-containing silica is particularly effective as an ultraviolet ray-shielding material when it is spherical silica having zinc oxide particles dispersed in a silica matrix, wherein the spectral transmittance of a paste in a thickness of 30 μm obtained by dispersing 3 parts by weight of the zinc oxide-containing spherical silica in 7 parts by weight of liquid paraffin by means of a three-roll mill, is at most 20% at a wavelength of 320 nm and at least 40% at a wavelength of 400 nm.

The spectral transmittance is measured as follows. To 3 parts by weight of the zinc oxide-containing spherical silica, 7 parts by weight of liquid paraffin is added, and the mixture is dispersed by means of a three-roll mill until it becomes uniform, whereby a paste will be obtained. This paste is sandwiched by quartz plates and adjusted to a thickness of 30 μm by e.g. a spacer, and the spectral transmittance of the paste adjusted to a thickness of 30 μm is measured using quartz plates+liquid paraffin (thickness: 30 μm) as a blank.

The transmittance at a wavelength of 320 nm is required to be at most 20%. The smaller the transmittance at this wavelength, the better the ultraviolet ray-shielding characteristic. If the transmittance is higher than 20%, the desired ultraviolet ray-shielding effect can not be obtained, when the silica is incorporated to e.g. cosmetics, such being undesirable. More preferably, the transmittance at a wavelength of 320 nm is at most 15%.

The transmittance at a wavelength of 400 nm is required to be at least 40%. If the transmittance is lower than 40%, transmittance of visible lights tends to be poor, and a transparent touch will be impaired when the silica is incorporated to e.g. cosmetics, and whiteness will be distinct, such being undesirable. More preferably, the transmittance at a wavelength of 400 nm is at least 50%.

When the silica is to be used as a material for cosmetics or as an additive to a resin or coating material, the pH of silica is desired to be substantially neutral at a level of from 7 to 9. When it is incorporated into cosmetics, if the pH is high, it is likely to cause a damage to the skin, such being undesirable. When the pH departs from the above range towards an acidic side or an alkaline side, it is likely to promote decomposition or aggregation of a substance simultaneously incorporated.

The particle size of zinc oxide contained in the zinc oxide-containing spherical silica is preferably from 0.005 to 0.5 μm. If the particle size exceeds 0.5 μm, the ultraviolet ray-shielding performance tends to be low, such being undesirable. If it is less than 0.005 μ, not only the ultraviolet ray-shielding performance tends to be low, but also the wavelength region which can be shielded, tends to shift towards a short wavelength side, such being undesirable. The average particle size of zinc oxide is more preferably from 0.02 to 0.3 μm. The content of zinc oxide is preferably from 10 to 70 wt % of the entirety.

The average particle size of the zinc oxide-containing silica is preferably from 1 to 50 μm. In the present invention, spherical means that when the contour of silica is inspected by e.g. a scanning electron microscope, the majority of silica particles show substantially spherical shapes. Accordingly, it does not necessarily mean only the true spherical shape.

The zinc oxide-containing spherical silica having the above-mentioned light absorption characteristics can be prepared also by impregnating a compound containing zinc into fine pores of porous spherical silica produced by a known method and decomposing it to zinc oxide by a known method for supporting. In such a case, after supporting, heat treatment may be carried out to improve the ultraviolet ray-shielding performance.

However, it is preferred to disperse zinc oxide in an alkali metal silicate solution or a silica sol, followed by gelation with e.g. an acid, whereby zinc oxide can be dispersed more uniformly in a silica matrix. Especially when the process of the present invention is employed, a product having the above-mentioned light absorption characteristics can be easily obtained.

An ultraviolet ray-shielding material made of the zinc oxide-containing spherical silica of the present invention can be suitably incorporated to conventional cosmetics such as foundations, milky lotions, lotions, creams, lip sticks, eye shadows, body powders, perspiration controlling agents, shampoos or rinsing liquids. Cosmetics having such zinc oxide-containing spherical silica incorporated, have features such that the ultraviolet ray-shielding effects are high, the effects last for a long period of time, the possibility of decomposition of other components incorporated to the cosmetics is low, and the feeling in use such as smoothness or spreadability is excellent.

Further, a product having the surface of the zinc oxide-containing spherical silica coated with an oxide or hydroxide of a metal such as Si, Al or Zr, or with a resin such as nylon, polyethylene or polypropylene, may also be suitably incorporated.

A product having the surface of the zinc oxide-containing spherical silica or the surface of the above-mentioned coated product treated by silicone oil, a silane coupling agent, a titanate coupling agent, an alcohol, a surfactant, or other surface treating agent or surface modifier, is preferred, since the lasting effect of a cosmetic will be improved when it is incorporated to the cosmetic, and when the one treated by a coupling agent, is incorporated to a resin, the strength will be improved, or the dispersion stability will increase.

Further, by incorporating a ultraviolet ray-shielding material made of the zinc oxide-containing spherical silica of the present invention to e.g. a resin or coating material, the ultraviolet ray resistance will be improved, and the substrate can be protected from ultraviolet rays. Further, the spherical silica having zinc oxide supported thereon does not substantially decompose other components simultaneously incorporated.

Now, the present invention will be described in further detail with reference to Examples. However, it should be understood that the present invention is by no means restricted by such specific Examples.

EXAMPLE 1

Into an aqueous sodium silicate solution prepared by diluting 288.4 g of water glass ($SiO_2$ concentration: 29 wt %, molar ratio of $SiO_2/Na_2O$: 3.3) with 87.3 g of pure water, 45 g of zinc oxide having an average particle size of 0.26 μm, was added, and 240 ml of the mixture was stirred and dispersed for 10 minutes by a homomixer. This dispersion was put into a solution having 3.36 g of sorbitan monooleic acid ester dissolved in 960 ml of trichlorofluoroethane, and the mixture was emulsified by a homomixer, whereby a W/O type emulsion was obtained, and the average particle size of the sodium silicate aqueous solution was about 6 μm.

Into this emulsion, carbon dioxide gas diluted with air ($CO_2$ concentration: 10 vol %) was blown for gelation. The initiation time for gelation was 5.5 minutes. After blowing carbon dioxide gas for 15 minutes, trichlorofluoroethane was separated to obtain a slurry comprising spherical silica and water. This slurry had a pH of 9.0.

This slurry was filtered, and the obtained cake was washed with a saturated carbonic acid aqueous solution (pH=3.3) in an amount of 100 times the solid content and then dried. The obtained zinc oxide-containing spherical silica had a zinc oxide content of 32 wt %, a pH of 7.3 and an average particle size of 5.5 μm. To determine the pH of silica, 5 g of the silica was put into 45 g of pure water, followed by stirring for 10 minutes, and then the pH of the slurry was measured.

EXAMPLE 2

The slurry immediately after preparation as obtained in Example 1 was filtered, and the cake thereby obtained was slurried again by an addition of pure water in an amount of 20 times the solid content. Then, carbon dioxide gas was blown thereinto to bring the pH to 6.0, followed by filtration. This operation was repeated five times, and then the product was dried. The obtained zinc oxide-containing spherical silica had a zinc oxide content of 31 wt %, a pH of 7.2, and an average particle size of 5.5 μm.

EXAMPLE 3

Zinc oxide-containing spherical silica was prepared in the same manner as in Example 1 except that zinc oxide having an average particle size of 0.04 μm was used as zinc oxide. However, even when carbon dioxide gas was introduced under the same condition, the initiation time for gelation was 6 minutes. The obtained zinc oxide-containing spherical silica had a zinc oxide content of 31 wt %.

EXAMPLE 4

Zinc oxide-containing spherical silica was prepared in the same manner as in Example 1 except that the concentration of carbon dioxide gas was changed to 80 vol %, and the initiation time for gelation was changed to 3 minutes. This zinc oxide-containing spherical silica had a zinc oxide content of 33 wt %.

EXAMPLE 5

Zinc oxide-containing spherical silica was prepared in the same manner as in Example 3 except that the concentration of carbon dioxide gas was changed to 80 vol %, and the initiation time for gelation was changed to 3 minutes. This zinc oxide-containing spherical silica had a zinc oxide content of 32 wt %.

Evaluation of the ultraviolet ray-shielding characteristics 3 g of the zinc oxide-containing spherical silica obtained in one of Examples 1 and 3 to 5 and 7 g of liquid paraffin were mixed and dispersed by means of a three-roll mill. The paste thereby obtained was sandwiched between quartz plates and adjusted to a thickness of 30 μm. Then, transmittance was measured by an automatic recording spectrophotometer U-4000, manufactured by Hitachi Ltd. The transmittances at the respective wavelengths are shown in Table 1. 400 nm represents the visible light region, and 320 nm represents the ultraviolet light region. The smaller the transmittance, the better the ultraviolet ray-shielding characteristics. All of the zinc oxide-containing spherical silica showed higher absorbance in the ultraviolet ray region than in the visible light region. As compared with Examples 4 and 5, Examples 1 and 3 showed particularly good characteristics.

TABLE 1

| | Transmittances at the respective wavelengths (%) | |
|---|---|---|
| | 400 nm | 320 nm |
| Example 1 | 50.5 | 10.0 |
| Example 3 | 61.9 | 10.7 |
| Example 4 | 90.9 | 79.6 |
| Example 5 | 82.6 | 50.9 |

EXAMPLE 6

The slurry immediately after preparation in Example 1 was filtered, and the cake thereby obtained was washed with water in an amount of 100 times the solid content and dried. The obtained zinc oxide-containing spherical silica had a zinc oxide content of 32 wt % and a pH of 10.3. The pH was higher than in Examples 1 and 2, although the same amount of water was used.

EXAMPLE 7

Dilute sulfuric acid was added to the slurry immediately after preparation in Example 1 to bring the pH to 5, followed by filtration. The cake was washed with pure water in an amount of 100 times the solid content and dried. The obtained zinc oxide-containing spherical silica had a zinc oxide content of 25 wt % and a pH of 7.5.

EXAMPLE 8

The slurry immediately after preparation in Example 1 was filtered, and the cake thereby obtained was washed with dilute hydrochloric acid (pH=3.7) in an amount of 100 times the solid content and dried. The obtained zinc oxide-containing spherical silica had a pH of 9.7. The pH was higher than in Examples 1 and 2, although the same amount of water was used.

Zinc concentration in a waste liquid

With respect to Examples 1, 2 and 7, washing waste liquids (inclusive of the initial filtrate) were all mixed, and the zinc concentration was obtained by an EDTA method. The results are shown in Table 2. As compared with Examples 7, the zinc concentrations in the waste liquids were very small in Examples 1 and 2.

TABLE 2

| | Average zinc concentration in all waste liquids |
|---|---|
| Example 1 | 19 ppm |
| Example 2 | 33 ppm |
| Example 7 | 660 ppm |

EXAMPLE 9

Components (1) to (4) as identified in Table 3 were thoroughly mixed, and about one half of component (7) and component (8) were added thereto. The mixture was uniformly dispersed by a homomixer, and then components (5) and (6) and the remaining amount of component (7) were heat-melted and added thereto, and the mixture was thoroughly mixed. The mixture was poured into a container and cooled for solidification to obtain a foundation having a high ultraviolet ray-shielding effect and presenting a good feeling in use. The dispersion stability after one month was good, and there was no color change or no generation of abnormal odor.

TABLE 3

| | Components | Parts by weight |
|---|---|---|
| (1) | Zinc oxide-containing spherical silica of Example 1 | 30.0 |
| (2) | Talc | 8.0 |
| (3) | Sericite | 8.0 |
| (4) | Colored pigment | 1.9 |
| (5) | Solid paraffin | 5.5 |
| (6) | Carnauba wax | 3.3 |
| (7) | Liquid paraffin | 40.0 |
| (8) | Sorbitan monooleate | 3.3 |

COMPARATIVE EXAMPLE 1

A foundation was prepared in the same manner as in Example 9 except that the zinc oxide-containing silica of Example 1 was changed to zinc oxide-containing spherical silica (zinc oxide content: 32 wt %, pH 7.5) having a transmittance of 61.9% at 400 nm and 10.7% at 320 nm. The ultraviolet ray-shielding effect was substantially the same, but the transparent touch after coating on the skin decreased.

COMPARATIVE EXAMPLE 2

Zinc oxide-containing spherical silica was prepared in the same manner as in Example 1 except that the washing condition was changed to bring the pH to 10.3. The content of zinc oxide was 32 wt %, and the transmittance was 50.5% at 400 nm and 10.0% at 320 nm. Using this zinc oxide-containing spherical silica, a foundation was prepared in the same manner as in Example 9. The ultraviolet ray-shielding effect and the feeling in use were good, but upon expiration of one month, aggregates were partially observed.

EXAMPLE 10

Powder components (1) to (6) as identified in Table 4 were mixed and pulverized. The mixture was transferred to a Henschel mixer, and then the remaining components (7) and (8) were added and mixed to obtain a uniform mixture. The mixture was sieved to adjust the particle size, and then the mixture was press-compacted into a metal dish to obtain a compacted powder foundation having a high ultraviolet ray-shielding effect and presenting a good feeling in use.

TABLE 4

| | Components | Parts by weight |
|---|---|---|
| (1) | Talc | 32.0 |
| (2) | Sericite | 30.0 |
| (3) | Mica | 10.0 |
| (4) | Magnesium stearate | 1.0 |
| (5) | Zinc oxide-containing spherical silica of Example 3 | 15.0 |
| (6) | Colored pigment | 2.0 |
| (7) | Octyl dodecanol | 4.0 |
| (8) | Silicone oil | 6.0 |

EXAMPLE 11

The zinc oxide-containing spherical silica of Example 1 was subjected to hydrophobic treatment with methylhydrogen polysiloxane. Using this hydrophobic treated silica, a group of components (1) to (7) as identified in Table 5, a group of components (8) and (9) and a group of components (10) to (12) were respectively separately heated and mixed. Then, these mixtures were mixed, and component (13) was added thereto, followed gradual cooling. The mixture was emulsified by a homomixer to obtain a liquid foundation having a high ultraviolet ray-shielding effect and presenting a good feeling in use and perspiration resistance.

TABLE 5

| Components | | Parts by weight |
|---|---|---|
| (1) | Stearic acid | 3.0 |
| (2) | Isopropyl myristate | 9.0 |
| (3) | Liquid paraffin | 1.5 |
| (4) | Cetanol | 1.0 |
| (5) | Butyl parabene | 0.1 |
| (6) | Colored pigment | 2.0 |
| (7) | Hydrophobic treated zinc oxide-containing spherical silica | 8.0 |
| (8) | Triethanolamine | 1.5 |
| (9) | Purified water | 25.0 |
| (10) | Propylene glycol | 5.0 |
| (11) | Anticeptics | 0.2 |
| (12) | Purified water | 28.7 |
| (13) | Bentonite (1% aqueous solution) | 15.0 |

What is claimed is:

1. A process for producing zinc oxide-containing spherical silica, which comprises emulsifying in an organic solvent an aqueous alkali metal silicate solution comprising a surfactant, of from 10 to 70 wt %, based on the total amount of zinc oxide and $SiO_2$, zinc oxide with a particle size of from 0.005 to 0.5 μm, and then gelling the resulting emulsion with carbon dioxide gas.

2. The process for producing zinc oxide-containing spherical silica according to claim 1, wherein the gelation is conducted under such a condition that the initiation time for gelation would be at least 4 minutes.

3. The process for producing zinc oxide-containing spherical silica according to claim 1, wherein in the aqueous alkali metal silicate solution, the alkali metal is sodium, the molar ratio of $SiO_2/Na_2O$ is from 2.0 to 3.5, and the concentration of the aqueous solution is from 5 to 30 wt % as $SiO_2$.

4. The process for producing zinc oxide-containing spherical silica according to claim 1, wherein the organic solvent is an organic solvent in which carbon dioxide gas is soluble.

5. The process for producing zinc oxide-containing spherical silica according to claim 1, wherein the organic solvent is at least one member selected from the group consisting of aliphatic hydrocarbons, aromatic hydrocarbons, chlorinated hydrocarbons and chlorofluorocarbons.

6. The process for producing zinc oxide-containing spherical silica according to claim 1, wherein the spherical silica formed by the reaction is washed with water having carbon dioxide gas dissolved therein.

7. The process for producing zinc oxide-containing spherical silica according to claim 6, wherein the pH of the water having carbon dioxide gas dissolved therein is from 3.3 to 4.

8. The process for producing zinc oxide-containing spherical silica according to claim 1, wherein the spherical silica formed by the reaction is slurried, and then carbon dioxide gas is blown into the slurry to adjust the pH to a level of from 5 to 7, followed by filtration, and this operation is carried out at least once.

9. The process for producing zinc oxide-containing spherical silica according to claim 8, wherein the operation is carried out until the pH of a 10 wt % slurry obtained by dispersing the zinc oxide-containing spherical silica in water, becomes from 7 to 8.

* * * * *